United States Patent [19]

Tsuno et al.

[11] Patent Number: 4,576,145
[45] Date of Patent: Mar. 18, 1986

[54] FIBERSCOPE

[75] Inventors: Koichi Tsuno; Akira Nishimura, both of Osaka, Japan

[73] Assignee: Sumitomo Electric Industries, Ltd., Osaka, Japan

[21] Appl. No.: 582,517

[22] Filed: Feb. 22, 1984

[30] Foreign Application Priority Data

Feb. 22, 1983 [JP] Japan .................................. 58-27875

[51] Int. Cl.⁴ .............................................. A61B 1/06
[52] U.S. Cl. ...................................................... 128/6
[58] Field of Search .......................... 128/3, 4, 5, 6, 7; 350/96.26

[56] References Cited

U.S. PATENT DOCUMENTS 4,445,892  5/1984  Hussein et al. ..................... 128/4 X
4,448,188  5/1984  Loeb ....................................... 128/6

Primary Examiner—William H. Grieb
Attorney, Agent, or Firm—Sughrue, Mion, Zinn, Macpeak & Seas

[57] ABSTRACT

A fiberscope, particularly, a fiberscope adapted to be inserted into a blood vessel or the like, having a reduced diameter and reduced flow rate of flushing fluid. A cylindrically shaped inflatable balloon is disposed around the flexible tube of the fiberscope somewhat rearward of the tip end. When an observation is to be performed, the balloon is inflated to reduce the flow rate of blood in the vessel. As a result, the amount and flow rate of the flushing fluid needed to provide a clear visual field between the tip of the fiberscope and the wall of the vessel to be observed are reduced.

3 Claims, 6 Drawing Figures

FIBERSCOPE

BACKGROUND OF THE INVENTION

The present invention relates to a fiberscope. More particularly, the invention relates to a fiberscope which is adapted to be inserted into a bodily passage, such as a blood vessel or the like, through which an opaque fluid, such as blood, passes to observe the interior of the passage.

A conventional fiberscope of the same general type to which the invention pertains, as shown in FIGS. 1 and 2, includes an illuminating light carrying optical fiber 7 passing through a flexible tube 1 to direct light from a light source 3 to a blood vessel wall 5, an image light receiving optical fiber 11 for directing light reflected from an image of the blood vessel wall and received through an optical system at the end thereof to an eyepiece assembly 9, and a liquid guiding passage 17 for guiding a transparent flushing liquid such as a normal saline solution from a syringe 15 to the tip of the fiberscope to form a transparent region between the blood vessel wall 5 and the tip of the fiberscope. Reference numeral 19 designates a branching mount.

The flushing liquid which forms the transparent region should be supplied at a flow rate $Q_F$ at least equal to the flow rate $Q_B$ of blood, that is, about 50 cm$^3$/sec. For example, where a blood vessel has an inner diameter of 10 mm, the blood flows at a speed of 64 cm/sec. In this instance, if it is desired to obtain a clear visual field for 0.5 sec., the required volume of the flushing liquid is 25 cm$^3$. However, injection of such a large quantity of normal saline solution into the blood vessel in such a period of time may create a shock force which damages the vessel, while further the high pressure required to inject the solution might possibly force dissolved gas out of the solution, which is of course dangerous. For example, the initial velocity of the saline solution jetted from a flushing tube of an inner diameter of 3 mm is about 7 m/sec. This causes a strong shock to the blood vessel. Moreover, if a large quantity of normal saline solution is to be injected, the liquid guide passage must have a large cross section. This causes the overall diameter of the fiberscope tube to be large, resulting in disadvantages in that difficulties are then encountered in inserting the tube into the blood vessel to be examined.

SUMMARY OF THE INVENTION

It is a primary object of the invention to remedy the shortcomings noted above. To this end, a fiberscope according to the invention, which is adapted to be inserted into a bodily passage through which an opaque liquid passes for observing the interior of the passage, includes a light carrying optical fiber passing through a flexible tube to direct light from a light source to the object to be observed, an image receiving optical fiber for conveying an image of the object to viewing means, and a liquid guide passage for guiding a transparent flushing liquid and to jet the latter from the tip of the tube. In accordance with an important aspect of the invention, an expandable balloon is provided rearwardly of the tip of the tube around the side wall of the tube, and a fluid passage for inflating the balloon is provided in the tube in communication with the interior of the balloon to thereby inflate the balloon when an observation is to be made to temporarily slow the flow of the opaque fluid, thereby to minimize the flow rate of the flushing liquid required for a visual field formation.

DESCRIPTION OF THE PREFERRED EMBODIMENTS

Details of the invention will be hereinafter explained with reference to the accompanying drawings in which a preferred embodiment of the invention is shown.

Figure 1:
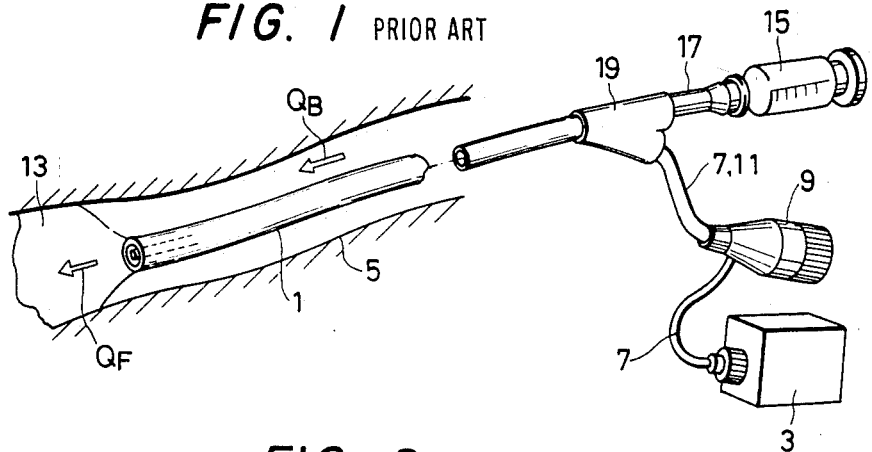
FIG. 1 is a perspective view showing a conventional fiberscope.
Figure 2:
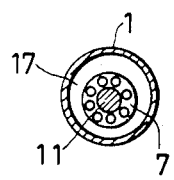
FIG. 2 is a cross-sectional view of a portion of the fiberscope shown in FIG. 1 inserted into a blood vessel.
Figure 3:
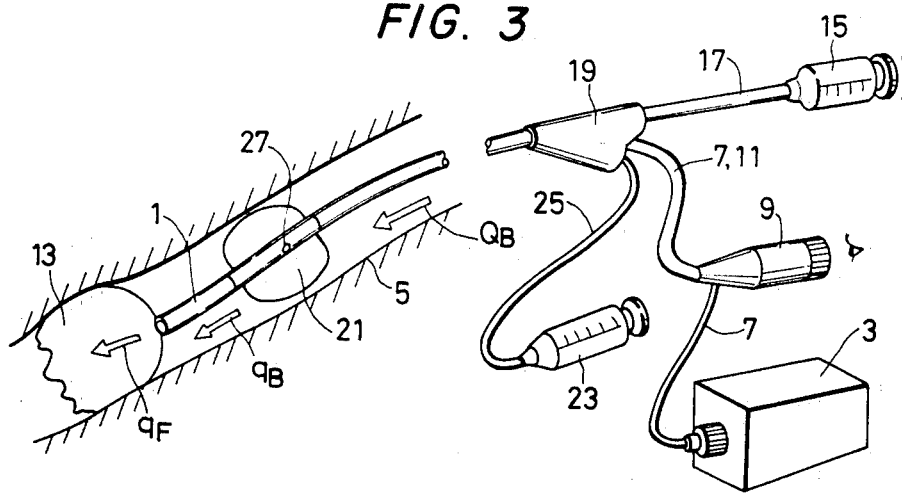
FIG. 3 is a view similar to FIG. 1 but showing a fiberscope according to the present invention.
Figure 4:
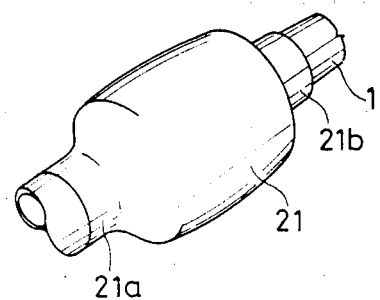
FIG. 4 is a perspective view showing a mounting structure of a balloon.
Figure 5:
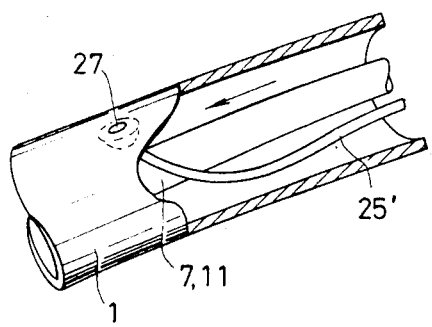
FIGS. 5 and 6 are perspective views showing a configuration of a fluid passage used for inflating the balloon.

FIGS. 3 through 6 show an embodiment of the invention applied to an intravascular observing fiberscope, similar to the case of FIG. 1. In these figures, like reference numerals are used to designate like components in FIG. 1.

In accordance with the invention, an inflatable balloon 21 (see FIG. 4) is provided rearwardly of the tip of the tube from which a flow 13 of flushing fluid is jetted and around the side of the tube, and a fluid passage 27 is formed in the tube 1 to supply fluid for inflating the balloon. The inflating flush may, for instance, be carbon dioxide or normal saline supplied from a syringe 23 through a tube 25, 25' (see FIG. 5). The balloon 21 is mounted around the tube by fastening front and rear ends 21a and 21b of a cylindrically shaped elastic element with thread, heat-shrinkable tubing, or adhesive to form a fluid-tight engagement with the tube 1. Polyurethane, natural rubber, silicon rubber and the like can be employed as the material of the balloon 21.

Figure 6:
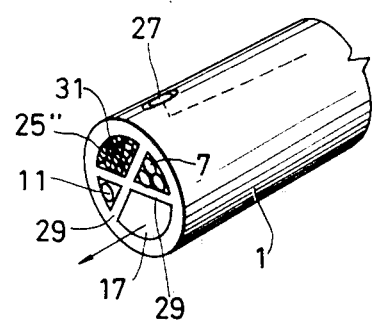

As an alternative to the tube 25, 25', the interior of the tube 1 can be divided by a plurality of longitudinally extending partition walls 29 into a plurality of passages, as shown in FIG. 6, one of the latter being an inflating fluid passage 25" for balloon inflation. In that case, the side wall of the tube at the balloon mounting portion is provided with a hole 27 in communication with the inflating passage. The inflating passage is blocked forwardly of the hole 27 with a filler 31, such as a resin or the like. The other passages into which the tube is divided by the partition walls 29 are available as passages for the light carrying optical fiber 7, the light receiving optical fiber 11, and the flushing liquid.

In the arrangement described above, the fluid for inflating the balloon is supplied from the syringe 23 to the balloon when the interior of the blood vessel is to be observed, to thus expand the balloon to a size such that the blood flow downstream of the balloon 21 is momentarily reduced to a flow rate $q_B$ less than the flow rate $Q_B$ upstream thereof. When the balloon has been inflated, the flushing liquid 13 is supplied from the syringe 15 at a flow rate $q_F$ required for providing a clear visual field. Since the blood flow rate $q_B$ is substantially reduced from $Q_B$, the flow rate $q_F$ can accordingly be made substantially less than $Q_F$. Hence, the total volume of the flushing liquid required is less than in the conventional arrangement, thereby reducing the shock force acting on the inner walls of the blood vessel and the surrounding tissue. The outer diameter of the tube 1 is also reduced, making possible easy insertion into blood vessels. If the balloon 21 is mounted in the proximity of the tip of the tube 1, the balloon 21 can be made to expand longitudinally, thus providing support for the tip of the tube centrally of the interior of the blood vessel.

As set forth hereinbefore, according to the invention, the required flushing liquid flow rate for forming a clear visual field is lowered to therefore minimize the total volume of the flushing liquid needed and the pressure at which the liquid is supplied. Thus, a fiberscope is obtained having greatly lessened ill effects on the body.

Although preferred embodiments have been described with reference to a fiberscope used for examining blood vessels, the invention is not limited thereto and is generally applicable to any fiberscope adapted to be inserted into a passage through which an opaque liquid or gas passes for observing the interior of the passage.

We claim:

1. A fiberscope adapted to be inserted into a passage through which an opaque liquid passes for observing the interior of said passage, comprising: a flexible tube; a first optical fiber passing through said flexible tube for carrying illuminating light from a light source to an object to be observed, said flexible tube having plural passages defined by longitudinally extending partitioning walls formed interior to said flexible tube; a second optical fiber for carrying image light reflected from said object to image viewing means; and liquid guiding passage means for guiding a transparent flushing liquid to a tip of said tube; an inflatable balloon provided rearwardly of said tip of said tube surrounding a portion of an outer wall of said tube; and fluid passage means for providing an inflating fluid to said balloon, said fluid passage means being disposed in said tube and communicating with said balloon, said fluid passage means comprising one of said plural passages.

2. The fiberscope according to claim 1, wherein said flexible tube is dimensioned to make said fiberscope suitable for an intravascular observation fiberscope.

3. The fiberscope according to claim 1, wherein said balloon is formed of a material selected from the group consisting of polyurethane, silicon rubber and natural rubber.

* * * * *